United States Patent [19]

Van Agthoven

[11] Patent Number: 5,627,213
[45] Date of Patent: May 6, 1997

[54] PREPARATION FOR LYSING ERYTHROCYTES

[75] Inventor: André Van Agthoven, Marseilles, France

[73] Assignee: Immunotech, Marseilles, France

[21] Appl. No.: 246,240

[22] Filed: May 19, 1994

[30] Foreign Application Priority Data

May 19, 1993 [FR] France .................... 93 06333

[51] Int. Cl.$^6$ .......... A61K 31/19; A61K 31/11; A61K 31/135; A61K 31/045
[52] U.S. Cl. .......... 514/557; 514/693; 514/694; 514/696; 514/724
[58] Field of Search ............. 514/693, 694, 514/696, 557, 724; 435/2

[56] References Cited

U.S. PATENT DOCUMENTS 4,902,613  2/1990  Chang et al. .................. 435/2

FOREIGN PATENT DOCUMENTS 0022670  1/1981  European Pat. Off. .
0161770  11/1985 European Pat. Off. .
0214613  3/1987  European Pat. Off. .
0530490  3/1993  European Pat. Off. .
8505640  12/1985 WIPO .
8905092  6/1989  WIPO .

OTHER PUBLICATIONS

A. Boyem. "Isolation of Leucocytes from Human Blood.", Isolation of Leucocytes from Human Blood Further Observations., A One-stage Procedure for Isolation of Granulocytes and Lymphocytes from Human Blood., Isolation of Mononuclear Cells and Granulocytes from Human Blood., Isolation and Removal of Lymphocytes from Bone Marrow of Rats and Guinea-pigs. The Scandinavian Journal of Clinical and Laboratory Investigation. (1967-68. Suppl. 94-101. 305.293$^B$).

Windholz et al., *The Merck Index*, 10th Ed. abstract No. 1513, p. 1507 (1983).

*Primary Examiner*—Kevin E. Weddington
*Attorney, Agent, or Firm*—Browdy and Neimark

[57] ABSTRACT

A preparation for lysing erythrocytes. characterized herein so far as the aqueous preparation with a substantially physiological ionic strength comprising a mixture:
of an aliphatic aldehyde,
of a polyhydric alcohol and,
of a salt of a strong acid and of an alkali metal or an alkaline earth metal.

31 Claims, 3 Drawing Sheets

PREPARATION FOR LYSING ERYTHROCYTES

FIELD OF THE INVENTION

The present invention includes a method and a preparation for the lysing of erythrocytes, the preparation of the blood, and a method to analyze erythrocytes.

BACKGROUND AND PRIOR ART

Blood contains several cell populations. The majority of them are erythrocytes and platelets. Erythrocytes function in the exchange and transport of carbon dioxide and oxygen. The platelets play a role in blood coagulation. The leukocytes are a minor population involved in the control of the immune system.

By microscopic analysis or by flow cytometric analysis, one can distinguish three subpopulations in the leukocyte population: polynuclear cells, having several nuclei and mononuclear cells having one nucleus, among which one can further distinguish lymphocytes with a small, round nucleus and monocytes with a larger moon-shaped nucleus.

Using cytometry, in a scatter analysis, one can distinguish these populations in a scattergram. In the leukocyte subpopulation, approximately 60% of the cells are polynuclear cells, approximately 30% are lymphocytes and approximately 10% are monocytes. Variation of the percentages of these subpopulations can be an indication of the state of health of an individual.

By the staining of blood cells with monoclonal antibodies conjugated to a fluorescent marker and after analysis of cells by microscopy or by flow cytometry one can distinguish blood cells and subpopulations more precisely and in more detail than by simple optic means.

For instance, using the marker CD19, one can distinguish B-cells in the lymphocyte population which are derived from bone marrow. In the same population one can distinguish, with the CD3 marker, T-cells which are derived from the thymus. With the CD4 and CD8 markers one can distinguish T-cells with a helper function or a suppressor/killer function, respectively.

The identification of lymphocyte sub-populations is important for the diagnosis or the treatment of diseases of the immune system.

Because the erythrocytes are a major population in the blood, they can mask leukocytes and make their analysis by flow cytometry difficult. Conventional immunofluorescence techniques include a physical separation of lymphocytes and erythrocytes, for instance by gradient density centrifugation (Boyem, A. 1968 Scand. J. Clin. Lab. Invest., 21 suppl. 97).

Another method, more rapid, is erythrocyte lysis in whole blood. For instance, in the method of Hansen (U.S. Pat. No. 4,284,412, EP-A-0.022.670), a sample of blood treated with an anticoagulant is mixed with a fluorescent antibody conjugate preparation. After incubation and lysis of the erythrocytes, the sample is passed in a flow cytometer, to analyze leukocyte populations which are positive for a certain antibody.

To perform a correct cytometric analysis, it is not only necessary to lyse all the erythrocytes, and one also has to conserve all the leukocytes in a morphological state in which the cytometer is capable of distinguishing between polynuclear cells, monocytes, lymphocytes and the mixture of cellular debris and platelets. Various methods of lysing erythrocytes exist. These methods may be based, for instance, on acid treatment, on alkaline treatment, treatment based on the use of ammonium chloride, polyhydric alcohols or on hypotonic shock. A problem with all these methods is that in lysing the erythrocytes, modifications are introduced in the leukocyte morphology.

In conventional methods, one limits the leukocyte degradation, for instance by analyzing the sample immediately after the lysis or by neutralization after acid and hypotonic conditions, or by washing the cells, or by addition of a fixing reagent such as formaldehyde or paraformaldehyde.

The methods of lysis used by the manufacturers of cytometers are adapted to the optical characteristics of the different cytometers. The cytometers of Becton, Dickinson and Co. are relatively insensitive to morphological changes of leukocytes. A lysis under slightly hypotonic conditions is indicated for this type of apparatus (U.S. Pat. No. 4,902,613). Cytometers of the Coulter company are much more sensitive to morphologic modification of the leukocytes. A lysing system from Coulter (WO-89/0509) applies hypotonic and acid lysis during six seconds approximately and corrects thereafter the isotonic value and the pH of the mixture. The inconvenience of such a system is that the exact six-second period is difficult to achieve under non-automatic conditions of operation.

Another method consists of the use of ammonium chloride. In this method, the ionic strength of the solution is physiologic and the leukocyte morphology is well conserved after a short period. The disadvantage of this method is that the ammonium chloride causes an intracellular rise of pH and a continuous degradation of leukocytes, even after the washing of the cells, which cannot be arrested with a fixing reagent.

It would be desirable to have a method of leukocyte analysis and of erythrocyte lysis which avoids washing of the samples and, therefore, inaccurate leukocyte counts.

SUMMARY OF INVENTION

Therefore, the object of the present invention is a preparation for lysing erythrocyte cells of a blood sample without the formation of interfering erythrocyte debris during the lysis. The lysing method according to the present invention guarantees a stable sample preparation with good separation of leukocyte subpopulations in a flow cytometry cytogram. The fluorescent properties of the subpopulations obtained by staining with conjugated antibodies are completely conserved during this procedure.

The object of the present application is a method characterized by lysing erythrocytes with the protection of leukocytes of a blood sample, which has been treated before with an anticoagulant and with an aqueous preparation of physiological ionic strength including:

an aliphatic aldehyde a polyhydric alcohol and a salt of a strong acid and of an alkali metal or an alkaline earth metal.

The above preparation will be called hereafter :"Lysing preparation".

The aliphatic aldehyde, in sufficient quantity and in association with the polyhydric alcohol, will lead to a fixation of all the leukocytes of the blood and to the lysis of the erythrocytes. This fixation is obtained by a cross-linking between the amino-terminal groups of the proteins of the cell walls.

By aliphatic aldehyde is meant, for instance, acetaldehyde, butyraldehyde, glyoxal and notably, formaldehyde and paraformaldehyde.

The concentration of an aliphatic aldehyde in the mixture of blood and the lysing preparation is preferably between 0.14 and 0.72M, and most preferably between 0.36 and 0.5 M; under 0.1M and above 0.72M, the leukocyte protection may be sufficient, but erythrocyte lysis will not be obtained.

The quantities of aliphatic aldehyde, notably formaldehyde, are given herein for a solution of aldehyde at 37% w/v (13.3M) stabilized with 10% methanol (3.12M).

The preparation, notably having a substantially physiological ionic strength according to the present invention, contains also a polyhydric alcohol such as ethylene glycol, diethylene glycol, polyethylene glycol and, preferably, glycerol.

The final concentration of the polyhydric alcohol in the mixture of blood and lysing preparation is preferably between 0.44 and 2.2M. The preferred concentration in the mixture is between 0.76 and 1.63M. Under a concentration of 0.44M, erythrocyte lysis is insufficient; above 2.2M, the erythrocytic debris augments in volume and starts to interfere with the lymphocyte population in the scattergram.

In order to obtain an ionic concentration which is substantially physiologic, one uses the salt of a strong acid, such as hydrochloric acid, sulphuric acid and, preferably, perchloric acid.

The alkali metal or alkaline earth metal associated with the strong acid is lithium, sodium, potassium, magnesium or calcium and, preferably, sodium.

The concentration of the strong acid such as the perchlorate, in the mixture of blood and lysing preparation, according to the invention, can be, for instance between 20 and 500 mM, and, preferably, between 40 and 300 mM. The adjustment of the ionic strength to a strength which is substantially physiologic is state of the art.

Surprisingly, in view of the fact that an aliphatic aldehyde, such as formaldehyde, by itself fixes leukocytes and that a polyhydric alcohol such as glycerol does not lyse erythrocytes, the association of the two compounds leads to a significant lysis of the erythrocytes.

Under the preferred conditions of the use of the above described method, the above described preparation includes also an aliphatic alcohol, notably with 1 to 6 carbon atoms such as ethanol, methanol, propanol, n-butanol and, preferably, isobutanol. The concentration of the aliphatic alcohol such as isobutanol in the mixture of blood and reagent is preferably between 0.01 M and 0.54 M, and most preferred, between 0.05 M and 0.22 M. Under 0.01 M the aliphatic alcohol is not efficient; above 0.54 M, the erythrocyte debris augments in volume in a way such that it interferes with the lymphocytes in the scattergram.

The polyhydric alcohols, the salts of alkali metals or of alkaline earth metals, all have a tendency to increase the volume of the erythrocyte debris.

To obtain a maximal conservation of the leukocyte morphology, the ionic strength of the above described preparation preferably has to be a physiological value. One may use a concentration equivalent to approximately 150 mM sodium chloride, for instance 150 mM±80%, preferably 150 mM±30% and most preferred 150 mM±10%.

The above described preparation preferably includes a low proportion of at least one weak acid. It is preferably present at a concentration of between approximately 10 and 100 mM, in the mixture of blood and lysing preparation, and most preferred at between 20 and 60 mM. The weak acid may, for instance, be one of the following acids; fumaric, malonic, oxalic, acetic, succinic, pyruvic, lactic, aconitic, formic, ascorbic, phosphoric, polyphosphoric, carbonic, tartaric and, notably, citric acid. By their position in the cytogram, the monocytes are particularly sensitive to the presence of alkaline earth metals in the lysing reagent. The presence of these components has a beneficial effect on the diffusion of monocytes in the scattergram. To obtain this effect, the presence of a small quantity of a metal, preferably of two alkaline earth metals, in the mixture of blood and the preparation is preferred. Examples of alkaline earth metals are manganese, calcium and magnesium. Preferably, one uses a mixture of magnesium and calcium salts. The concentration of magnesium can vary between 0.1 mM and 100 mM in the mixture of blood and reagent, and preferably between 3 mM and 60 mM. The concentration of calcium is notably between 0.1 and 100 mM in the mixture and, preferably, between 3 and 60 mM.

As counter ion of magnesium and calcium, a halogen, preferably chloride, is preferred. The pH of the mixture of blood and reagent has to be between 5 and 9, preferably between 6 and 8. The preferred pH is approximately 7.

The sample is brought in contact for at least 2 minutes with the preparation described above, preferably at least 5 minutes and, notably, approximately 10 minutes. It is possible to prolong the contact up to several hours without a notable loss of the quality of the analysis, which shows the excellent leukocyte stabilization in the mixture.

The object of the present invention is also an aqueous preparation for the lysis of erythrocytes and the protection of leukocytes, characterized by that it includes:

an aliphatic aldehyde a polyhydric alcohol a salt of a strong acid and an alkali metal or an alkaline earth metal and by that its ionic strength is physiologic, remembering that physiological ionic strength is equivalent to approximately 150 mM of sodium chloride.

The preferred preparations are those defined above within the scope of the preferred methods.

To be preferred is a preparation which is an aqueous solution being approximately 0.54 M in formaldehyde, approximately 1.36 M in glycerol, approximately 150 mM in sodium perchlorate, approximately 0.1 M in isobutanol, approximately 50 mM in sodium citrate, approximately 5 mM in magnesium chloride, approximately 5 mM in calcium chloride and at a pH of approximately 7.0.

A leukocyte analysis of a blood sample using the method of protection according to the invention is notably the following.

An 0.1 ml sample of blood, treated with an anticoagulant, is mixed with a preparation of one or two fluorescent conjugated antibodies, preferably in a volume of 20 μl after incubation, the mixture is combined with the preparation according to the invention. The preparation is specifically an aqueous solution of approximately 0.54 M of formaldehyde, approximately 1.36 M of glycerol, approximately 150 mM of sodium perchlorate, approximately 0.1 M of isobutanol, approximately 50 mM of sodium citrate, approximately 5 mM of magnesium chloride, approximately 6 mM of calcium chloride and at a pH of approximately 7.0.

The volume of the preparation, as used above, is, for instance, between 0.2 ml and 1 ml for 0.1 ml of sample and preferably approximately 0.5 ml for 0.1 ml of sample.

Immediately after combining, the mixture is vortexed and left at room temperature during a 10 minute period. Subsequently, the total volume of the mixture after lysis is, by preference, increased by the addition of a volume of 0.5 ml of a physiological solution of sodium chloride (0.9% weight by volume; i.e. 154 mM), buffered by 8 mM sodium phosphate at pH 7.2 in order to increase the volume of the sample, staying within physiological conditions. The lysis is considered as total after 10 minutes, after which the sample is ready for cytometric analysis.

The whole procedure is performed preferably at room temperature (18°–24° C.).

As mentioned above, the method of lysing whole blood according to the invention, has, according to the experience of the applicant, a limitation regarding the cytometry apparatus that is used. Cytometers of Coulter® Company such as Epics®, Profile® and Epics Excel®, and those using an optical system of the same type, are well adapted to a lysis of this sort. Other types of cytometers may give disappointing results.

The object of the present request is also a preparation of blood in which the erythrocytes have been lysed and the leukocytes have a substantially conserved morphology, characterized by the mixture of a blood sample treated with an anticoagulant and a lysing preparation as defined above.

The object of the present request is also a method of analysis of a leukocyte population of a blood sample in which a blood sample has been treated with an anticoagulant and subsequently, if desired, with antibodies specific for at least a population or subpopulations of leukocytes and subsequently with an erythrocyte-lysing agent. The method is characterized by the fact that after the treatment with the anticoagulant and, if desired, at least one labeled antibody, the sample is treated with an aqueous preparation of physiological ionic strength including:

an aliphatic aldehyde a polyhydric alcohol a salt of a strong acid and an alkali metal or alkaline earth metal and subsequently, preferably, after dilution of the sample using an isotonic diluting solution such as a physiological solution (0.9% w/v) of sodium chloride buffered with 10 mM sodium phosphate at pH 7.2 (PBS), the sample is submitted to cytometric analysis.

The above method can notably be employed under the preferential conditions described above.

BRIEF DESCRIPTION OF DRAWINGS

More specifically.

Figure 1A:
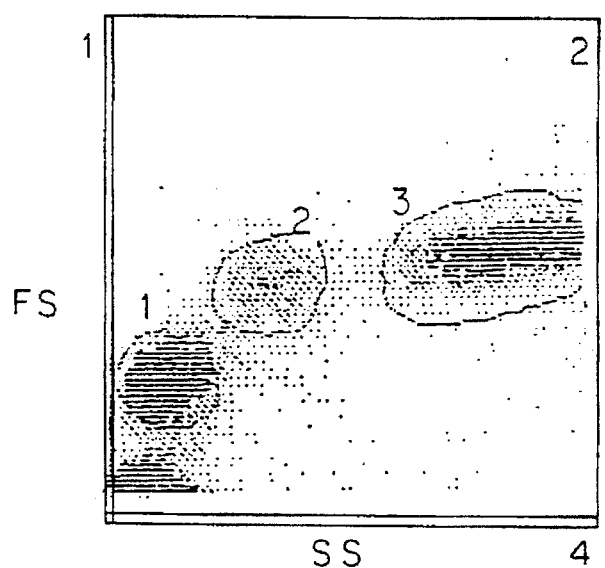
FIG. 1 shows the result of a scatter analysis (FIG. 1a) as well as double fluorescence diagrams (FIG. 1b to FIG. 1i) in cytograms which are obtained, using an Excel Epics Profil1 1®, of a whole blood sample, treated, using the preparation of example 1.
figure 1b represents a double fluorescence cytogram in the absence of fluorescent markers. The lymphocyte cells from scattergram "region" R1 are represented.
FIG. 1c represents a cytogram of the lymphocytes of whole blood in the presence of isotypic controls.
FIG. 1d represents whole blood lymphocytes labeled with CD45-FITC and CD14-PE.
FIG. 1e represents whole blood monocytes (region R2) labeled with CD45-FITC and CD14-PE.
FIG. 1f represents whole blood granulocytes (region R3), labeled with CD45-FITC and CD14-PE.
FIG. 1g represents whole blood lymphocytes labeled with CD3-FITC and CD4-PE.
FIG. 1h represents whole blood lymphocytes labeled with CD3-FITC and CD8-PE.
FIG. 1i represents whole blood lymphocytes labeled with CD3-FITC and CD19-PE.

The following examples illustrate the present invention without, however, being limiting.

EXAMPLE 1

Lysing Preparation

An aqueous lysing preparation, according to the invention, of the following composition was prepared;

| | |
|---|---|
| formaldehyde* | 0.54 M |
| glycerol | 1.36 M |
| sodium perchlorate | 0.150 M |
| isobutanol | 0.1 M |
| magnesium chloride | 0.005 M |
| calcium chloride | 0.005 M |
| sodium citrate | 0.05 M |
| distilled water | |
| pH = 7.0 | |

*formaldehyde stabilized with methanol.

EXAMPLE 2

Lysing Preparation

An aqueous lysing preparation, according to the invention, and having the following preparation.

| | |
|---|---|
| formaldehyde* | 0.36 M |
| glycerol | 1.36 M |
| sodium perchlorate | 0.150 M |
| isobutanol | 0.1 M |
| sodium fumarate | 0.05 M |

*formaldehyde is stabilized with methanol.

EXAMPLE 3

Samples of 0.1 ml of blood, treated with an anticoagulant, are distributed in 6 tubes.

To tube 1, 20 μl of PBS is added.

To tube 2, 20 μl of a mixture of two monoclonal antibodies (isotypic controls) with an irrelevant specificity, one conjugated to isothiocyanate (FITC) cat.No 0639 (10 μl), the other to phycoerythrin cat.#0670 (2 μl), and PBS (8 μl) are added.

To tube 3, 20 μl of a mixture of monoclonal antibodies having a CD45 specificity conjugated to FITC, cat.#0782 (2 μl), and of a monoclonal antibody with a CD14 specificity conjugated to phycoerythrin, cat.#0650 (2.5 μl), and PBS (15.5 μl) are added.

To tube 4, 20 μl of a mixture of monoclonal antibodies with a CD3 specificity conjugated to FITC cat.#1281 (2 μl), and an antibody with a CD4 specificity conjugated to PE cat.#0449 (10 μl) and PBS (8 μl are added.

To tube 5, 20 μl of a mixture of CD3-FITC cat.#1281 (2 μl), and CD8-PE cat.#0452 (3.3 μl) antibodies and PBS (14.7 μl) are added.

To tube 6, 20 μl of a mixture of antibodies CD3-FITC cat.#1281 (2 μl), CD19-PE antibody cat.#1285 (10 μl) and PBS (8 μl) are added.

The above mentioned antibodies are commercialized by Immunotech SA, in its product range "IOTEST". Comparable antibodies are commercialized by other companies.

After 20 minutes of incubation with the antibodies, 0.5 ml of the preparation of example 1 is added and the tubes are vortexed immediately. After 10 minutes of reaction, a volume of 0.5 ml of PBS is added to the tubes and the tubes are vortexed immediately.

After two hours at room temperature, the samples are analyzed by flow cytometry with an Epics Profile I cytometer from Excel. In the scatter analysis, a threshold is used to prevent counting of debris and platelets. A region is created around the populations of lymphocytes, monocytes and granulocytes. An analysis of fluorescence 1, detecting FITC-conjugates, and of fluorescence 2, detecting PE-conjugates, is effected on the lymphocyte cells in the region. Cells, positive in fluorescence for CD45 represent the leukocytes, permitting the distinction between leukocytes and debris plus platelets. Cells positive for CD14 are monocytes permitting the distinction between monocytes and lymphocytes; cells positive for CD3 and CD4 are helper T-cells. Cells positive for CD3 and CD4 are cytotoxic suppressor T-cells; cells positive for CD 19 are B-cells.

Figure 1B:
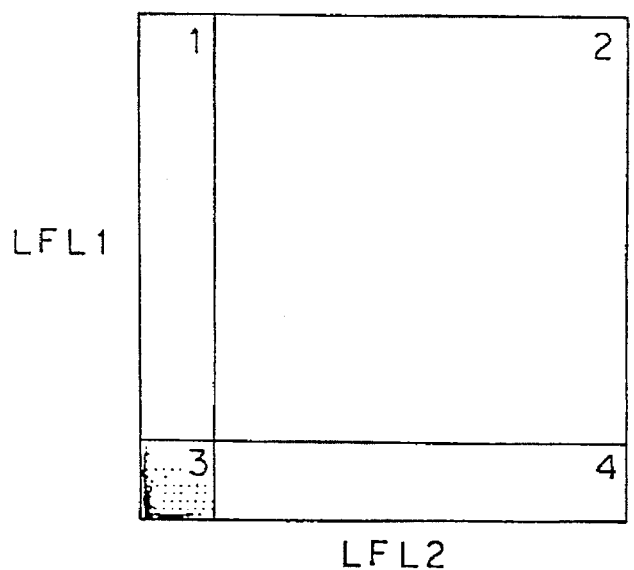
Figure 1C:
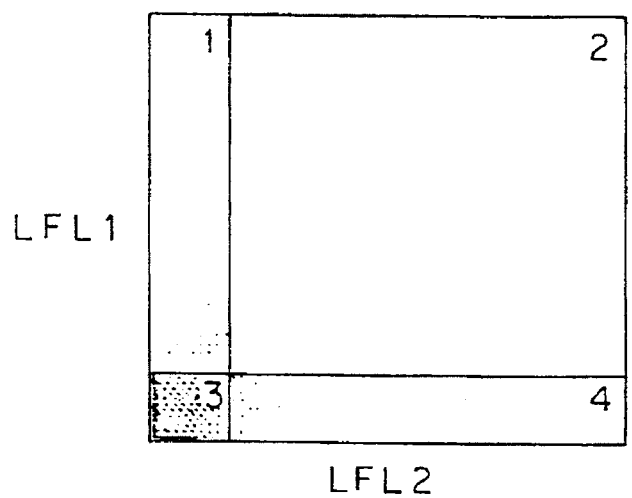
Figure 1D:
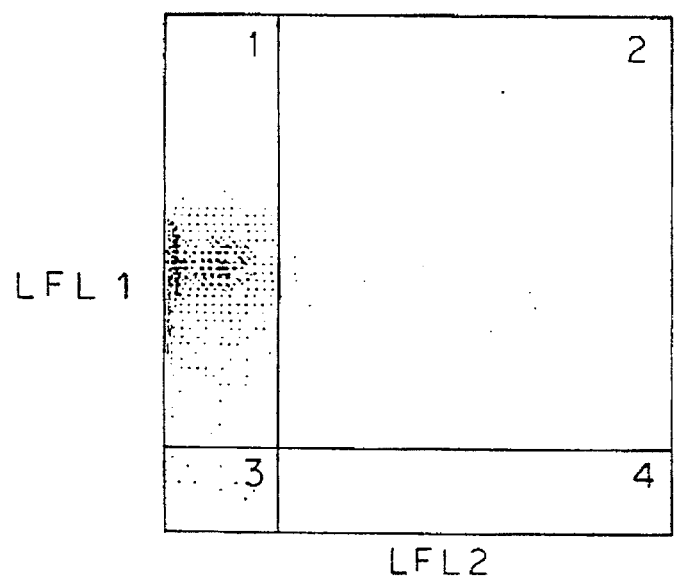
Figure 1E:
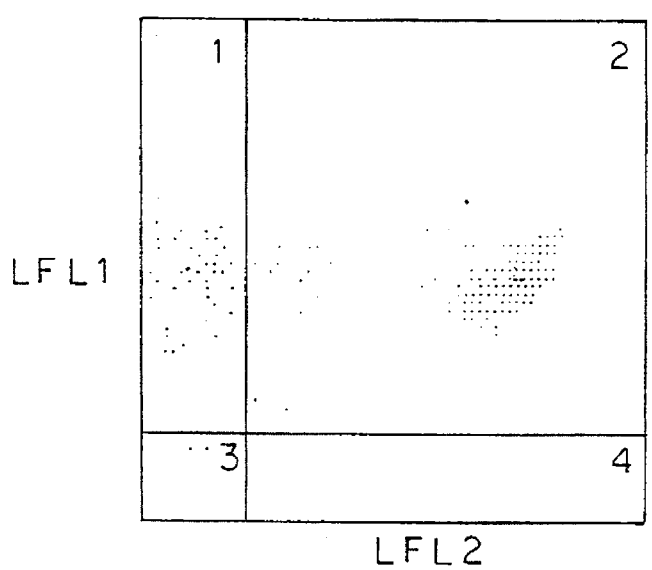
Figure 1F:
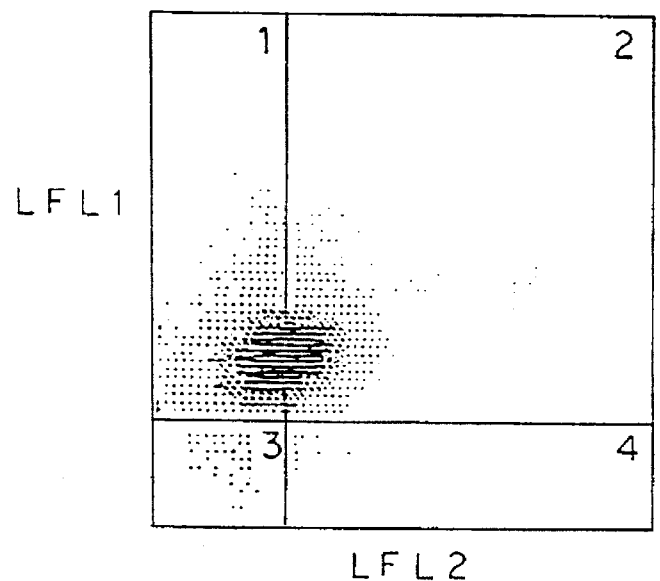
Figure 1G:
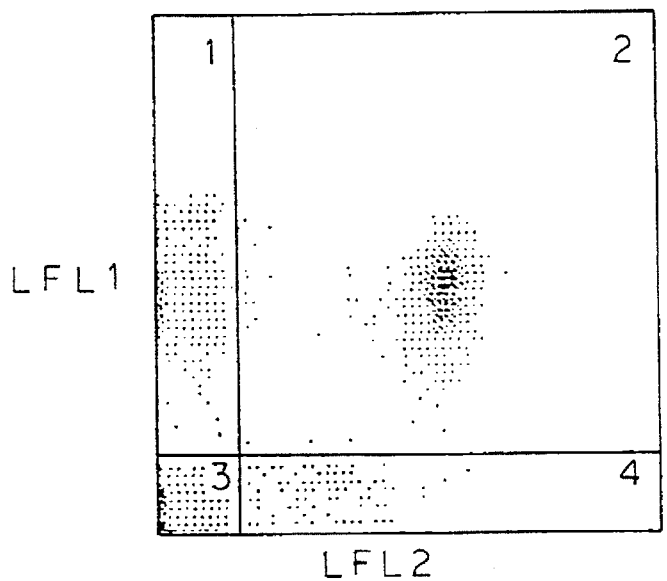
Figure 1H:
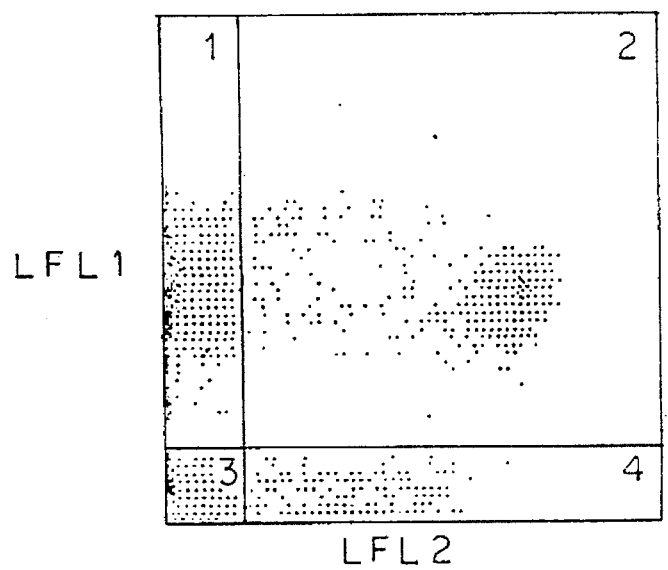
Figure 1I:
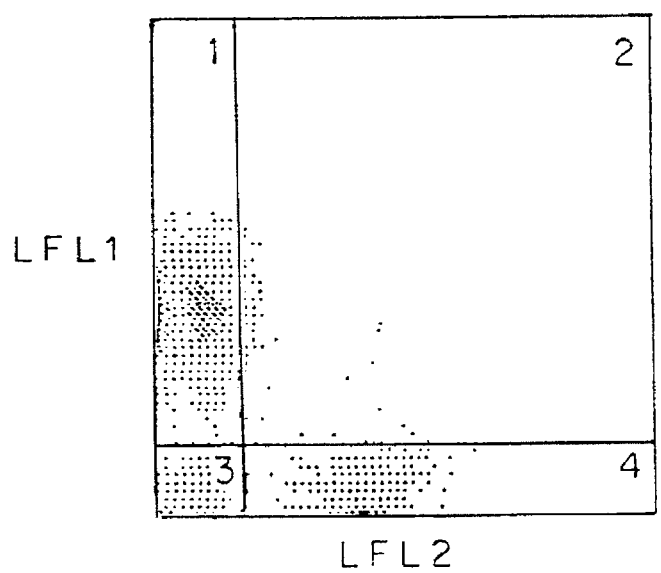

The results are presented in FIG. 1: The analysis shows that in the lymphocyte region, 99% of the events represent lymphocytes, 70% represent T-cells, 17% represent B cells and 12% represent non-T, non-B-cells.

The 70% of the T-cell population, is divided into 49% helper cells and 19% cytotoxic/suppressor cells.

In the monocyte region, 93% of the events represent monocytes. In the granulocyte region, 99% of the events represent granulocytes.

I claim:

1. A preparation for lysing erythrocytes, characterized herein insofar as it concerns an aqueous preparation with a substantially physiological ionic strength comprising a mixture:
   of an aliphatic aldehyde,
   of a polyhydric alcohol and,
   of a salt of a strong acid and of an alkali metal or an alkaline earth metal.

2. A preparation, according to claim 1, characterized herein insofar as:
   the aliphatic aldehyde is formaldehyde,
   the polyhydric alcohol is glycerol.

3. A preparation, according to claim 1, characterized herein insofar as the salt of a strong acid and of an alkali metal or alkaline earth metal is a perchlorate.

4. A preparation, according to claim 1, characterized herein insofar as it includes also an aliphatic alcohol.

5. A preparation, according to claim 1, characterized herein that it includes a small quantity of at least one salt of an alkaline earth metal, either magnesium or calcium.

6. A preparation, according to claim 2, characterized herein insofar as the salt of a strong acid and of an alkali metal or alkaline earth metal is a perchlorate.

7. A preparation, according to claim 6, characterized herein insofar as it includes also an aliphatic alcohol.

8. A preparation, according to claim 7, characterized herein that it includes a small quantity of at least one alkaline earth metal, either magnesium or calcium.

9. A preparation, according to claim 2, characterized herein insofar as it includes also an aliphatic alcohol.

10. A preparation, according to claim 9, characterized herein that it includes a small quantity of at least one alkaline earth metal, either magnesium or calcium.

11. A preparation, according to claim 3, characterized herein insofar as it includes also an aliphatic alcohol.

12. A preparation, according to claim 11, characterized herein that it includes a small quantity of at least one alkaline earth metal, either magnesium or calcium.

13. A preparation, according to claim 2, characterized herein that it includes a small quantity of at least one alkaline earth metal, either magnesium or calcium.

14. A preparation, according to claim 3, characterized herein that it includes a small quantity of at least one alkaline earth metal, either magnesium or calcium.

15. A preparation, according to claim 14, characterized herein that it includes a small quantity of at least one alkaline earth metal, either magnesium or calcium.

16. A preparation according to claim 11, wherein said aliphatic aldehyde is present in an amount sufficient to establish, in a mixture of said aqueous preparation and a sample of blood, a concentration of aliphatic aldehyde in the range between 0.14 and 0.72 M.

17. A preparation according to claim 16, wherein said concentration of said aliphatic aldehyde is in the range between 0.36 and 0.5 M.

18. A preparation, according to claim 1, wherein said polyhydric alcohol is present in an amount sufficient to establish, in a mixture of said aqueous preparation and a sample of blood, a concentration of polyhydric alcohol in the range of 0.44 and 2.2 M.

19. A preparation according to claim 18, wherein said concentration of said polyhydric alcohol is in the range between 0.76 and 1.63 M.

20. A preparation according to claim 3, wherein said salt of perchlorate and of an alkali metal or an alkaline earth metal is present in an amount sufficient to establish, in a mixture of said aqueous preparation and a sample of blood, a concentration of said salt of perchlorate and of an alkali metal or an alkaline earth metal in the range of 20 and 500 mM so as to provide a substantially physiologically ionic strength.

21. A preparation according to claim 20, wherein said concentration of said salt of perchlorate and of an alkali metal or an alkaline earth metal is in the range between 40 and 300 mM.

22. A preparation according to claim 11, wherein said aliphatic alcohol is present in an amount sufficient to establish, in a mixture of said aqueous preparation and a sample of blood, a concentration of aliphatic alcohol in the range between 0.01 and 0.54 M.

23. A preparation according to claim 22, wherein said concentration of aliphatic alcohol is in the range between 0.05 and 0.22 M.

24. A preparation according to claim 14, wherein said at least one salt of an alkaline earth metal is present in an amount sufficient to establish, in a mixture of said aqueous preparation and a sample of blood, a concentration of magnesium in the range between 0.1 mM and 100 mM.

25. A preparation according to claim 24, wherein said concentration of magnesium is in the range between 3 and 60 mM.

26. A preparation according to claim 14, wherein said at least one salt of an alkaline earth metal is present in an amount sufficient to establish, in a mixture of said aqueous preparation and a sample of blood, a concentration of calcium in a range between 0.1 and 100 mM.

27. A preparation according to claim 26, wherein said concentration of calcium is in the range between 3 and 60 mM.

28. A preparation according to claim 3, further comprising at least one weak acid.

29. A preparation according to claim 28, wherein said at least one weak acid is present in an amount sufficient to establish, in a mixture of said aqueous preparation and a sample of blood, a concentration of at least one weak acid in the range of between 10 and 100 mM.

30. A preparation according to claim 29, wherein said concentration of said at least one weak acid is in the range between 30 and 60 mM.

31. A preparation according to claim 6, wherein said formaldehyde is approximately 0.54 M, said glycerol is approximately 1.36 M, said perchlorate is approximately 150 mM sodium perchlorate, and further comprising approximately 0.1 M isobutanol, approximately 50 mM sodium citrate, approximately 5 mM magnesium chloride, and approximately 6 mM calcium chloride, and wherein said aqueous preparation has a pH of approximately 7.0.

* * * * *